United States Patent [19]
Ehlers et al.

[11] Patent Number: 6,040,503
[45] Date of Patent: Mar. 21, 2000

[54] BEAN-NUT POPPING BEANS

[75] Inventors: Jeffrey D. Ehlers, Moreno Valley; Mark H. Sterner, Riverside, both of Calif.

[73] Assignee: Appropriate Engineering and Manufacturing, Riverside, Calif.

[21] Appl. No.: 08/921,490

[22] Filed: Sep. 2, 1997

[51] Int. Cl.$^7$ .............................. A01H 5/00; A01H 5/10; A01H 1/04

[52] U.S. Cl. ........................... 800/313; 800/298; 800/260

[58] Field of Search ............................ 800/200, DIG. 23, 800/298, 313, 260; 47/58

[56] References Cited

PUBLICATIONS

Singh, et al., Races of Common Bean (*Phaselous vulgaris*, Fabaceae), *Economic Botany* 45:3 379–396 (1991).

"Lost Crops of the Incas:," *Little Known Plants of the Andes with Promise For Woldwide Cultivation* National Research Council Advisory Committee on Technology Innovation Board on Science and Technology for International Development, 3–15, (1989).

Shree P. Singh, "Patterns of Variation in Cultivated Common Bean (*Phaseolus vulgaris*, Fabaceae)," *Economic Botany*, 43(1), 39–57. (1989).

Spaeth, et al., "Microstructure of Nunas: Andean Popping Beans," (*Phaseolus Vulgaris* L), *Food Microstructure*, 8:263–269, (1989).

Zimmerer, Karl S., "Biological Diversity and Local Development: "Popping Beans" in the Central Andes,"*Mountain Research and Development*, 12(1):47–61, (1992).

http://www.xc.org/echo/aztext/azch3pul.htm#Rese, p. 4 and 5.

http://iubio.bio.indiana.edu/R30811–33133–/soft/usenet/bionet/plants/9310.newsm.

Tohmes et al. Variability in Andean nuna common beans (*Phaseolus vulgaris*, Fabaceae), Economic Botany, 49:78–95. 1995.

Van Beem et al. Nutritive value of the nuna popping bean, Economic Botany, 46:164–170. 1992.

Query Results: http://www.ars–grin.gov/cgi–bin/npgs/html/acc_query.pl, 1999.

*Primary Examiner*—Lynette R. F. Smith
*Assistant Examiner*—Melissa L. Kimball
*Attorney, Agent, or Firm*—Lyon & Lyon LLP

[57] ABSTRACT

A bean plant of the species *Phaseolus vulgaris* which exhibits the phenotypic characteristics of early maturity, bush type growth habit, synchronous fruiting, photoperiod insensitivity, and which produces a popping bean.

33 Claims, 1 Drawing Sheet

BEAN-NUT POPPING BEANS

FIELD OF THE INVENTION

This invention relates to a novel and distinct variety of a plant of the species *Phaseolus vulgaris* L., to the bean produced from such a plant and to the field of plant breeding.

BACKGROUND OF THE INVENTION

The following is a discussion of the relevant art, none of which is admitted to be prior art to the appended claims.

Healthy, minimally processed snack foods such as dried fruits and roasted or toasted nuts and cereals can have a positive impact on the average persons' diet and are an important and growing segment of the U.S. food industry. The development of toasted (not fried) snack foods from grain legumes are particularly desirable because these foods are naturally low in fat, and high in dietary fiber, protein, folic acid, and other nutrients. "Nuñas" are a class of common beans found in the Andean region of South America. On heating, nuñas pop or expand, producing a toasted, soft-textured edible product. Nunas are traditionally popped by rapidly heating them in a skillet with little or no oil (Zimmerer, 1992, *Mountain Research and Dev.* 12:47–61). Nuñas are presently cultivated in traditional farming systems as a climbing intercrop with maize (*Zea mays* L) by farmers in isolated pockets of Peru and Bolivia. Nuñas are adapted to cool, wet tropical highland areas, from 1,800 m to more than 2,800 m in elevation, and require 210 to 280 days to mature (Singh, 1989, *Econ. Botany* 43:39–57).

SUMMARY OF THE INVENTION

The present invention concerns a type of common bean (*Phaseolus vulgaris* L.) that rapidly expands (or "pops") upon heating, producing a toasted food which is softer in texture than a cornnut. In addition to being a tasty snack food item, "popping" beans could also have quality attributes useful to food processors, as for example, for energy-efficient preparation of "quick-cook" beans. The bean plants of the present invention possess early maturity, non-climbing growth habit, synchronous fruiting, photoperiod insensitivity and produce beans that possess the popping trait. In addition, the present invention concerns methods for producing such bean plants, and the popped bean product.

One advantage of the present invention is that the claimed popping bean varieties allow for high yields and economic production in the United States. The bean plants of the present invention can grow in the major bean growing regions in the United States including Idaho, North Dakota, Colorado, Michigan, Texas, California, and New York, i.e. any location where common beans (e.g., pinto, kidneys, small white, navy, etc.) are grown. Furthermore, the plants are capable of growth in any analogous climate worldwide.

The presently available accessions of nuñas will not produce grain under field conditions in the United States due to their late maturity (greater than 200 days) and extreme sensitivity to photoperiod. They do not flower when daylengths are about 12 ½ hours or longer. These factors cause the plant to flower too late to produce grain before the onset of cold weather in the Fall. Furthermore, the aggressive climbing growth habit and asynchronous fruiting makes them unsuitable for mechanized farming and once-over harvesting as is practiced in the United States.

In a first aspect, the invention features a bean plant of the species *Phaseolus vulgaris* which exhibits the phenotypic characteristics of early maturity, bush type growth habit, synchronous fruiting, photoperiod insensitivity, and which produces a popping bean.

Days to maturity are measured from planting to harvest. By "early maturity" it is meant that the plant reaches the dry pods stage in less than 200 days, and preferably in 90 days (+ or − 5 days).

By "bush type growth habit" is meant compact in growth. Growth can either be determinant or indeterminant. In bush determinant growth the terminals of the plant end in reproductive organs (pods) and the plants generally attain a height of approximately 0.5 meters. In bush indeterminant growth the terminals remain vegetative and plants typically attain a height no greater than 0.75 meters. Bush type growth habit is in contrast to the characteristic aggressive climbing (twining) indeterminant growth displayed by nuñas, which are typically grown as intercrop with maize and often reach the top of the maize plant. Such plants often reach a height of 3 meters. Because these plants continue to grow, flowering and poding appear together. Nuñias begin fruiting at higher nodal positions on the mainstem and branches and there are more vegetative branches than plants that exhibit bush determinant or bush indeterminant growth. The plants of claimed invention do not exhibit flowers and dry pods together under normal growing conditions (i.e., when pod setting is normal).

By "synchronous fruiting" is meant that an individual plant produces a single flush of flowers of about two to three weeks duration followed by pod filling and uniform pod maturation. Concentrated flowering and fruiting periods allows for efficient "once-over" harvesting of the bean crop.

By "photoperiod insensitivity" is meant that the photoperiod response with respect to reproductive development of the plants is essentially eliminated. The plants are day neutral and can flower in day lengths longer than 13 hours.

By "popping bean" is meant a bean that changes texture and volume when subject to heat within a given range of moisture, time and pressure. A popped bean has a visible expansion in size and a detectable softening in texture compared with an unpopped bean. The conditions necessary to produce popping are known to those who practice the art. Beans can be popped by a variety of methods including: frying in oil, exposure to hot air, rotating on a hot sandbed, or rotary infrared. The beans produced by the plants of the present invention exhibit popping that is at least comparable to that exhibited by nuñas.

In preferred aspects: early maturity is a growing season of no greater than 100 days in which the plant reaches the dry pod stage; the photoperiod insensitivity is the ability to flower when daylengths are greater than or equal to 13 hours; and the bush type growth habit encompasses a height of less than 0.75 meter.

In a second aspect the invention features plant parts derived from a plant of claims 1–4 including leaves, stem, pollen, plant cells and seed.

In a third aspect, the invention cultivating the plant of claims 1–4.

In a fourth aspect, the invention features a seed produced from the plant of claims 1–4.

In a fifth aspect, the invention features a bean seed of the species *Phaseolus vulgaris* capable of germinating into a plant which exhibits early maturity, bush type growth habit, synchronous fruiting, photoperiod insensitivity, and which produces a popping bean.

In a sixth aspect, the invention features a bean seed produced by a cross of a nuña accession and a *Phaseolus*

*vulgaris* cultivar exhibiting the characteristics of early maturity, bush type growth habit, synchronous fruiting, photoperiod insensitivity.

In preferred embodiments the nuña accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI6 608402; the *Phaseolus vulgaris* cultivar is selected from the group consisting of small white, small red, navy, dark red kidney, light red kidney, black or black turtle, pink, pinto, cranberry, and canario.

In a seventh aspect the invention features a bean seed produced by a first cross of a first nuña accession and a *Phaseolus vulgaris* cultivar exhibiting the characteristics of early maturity, bush type growth habit, synchronous fruiting, and photoperiod insensitivity; a second cross of a second nuña accession and the *Phaseolus vulgaris* cultivar exhibiting the characteristics of early maturity, bush type growth habit, synchronous fruiting, photoperiod insensitivity; and a third cross of the offspring of the first and second crosses.

In preferred embodiments, the first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402; the *Phaseolus vulgaris* cultivar is selected from the group consisting of small white, small red, navy, dark red kidney, light red kidney, black or black turtle, pink, pinto, cranberry, and canario.

In an eight aspect, the invention features a bean seed produced by a first cross of the Nuña accession No. PI316013 and a California Early Light Red Kidney line; a second cross of the Nuña accession No. PI316032 and a California Early Light Red Kidney line; and a third cross of the offspring of the first and second crosses.

In a ninth aspect, the invention features a bean suitable for popping produced from a species *Phaseolus vulgaris* which exhibits early maturity, bush type growth habit, synchronous fruiting, and photoperiod insensitivity.

In a tenth aspect, the invention features a popped bean from the species *Phaseolus vulgaris* that exhibits a texture less than that exhibited by a corn nut.

By "texture" is meant the shear force or compression or combination of the two required to deform the surface of a bean. The texture of a popped bean of the claimed invention is less than the texture exhibited by a cornnut, that is the shear force or compression or combination of the two is less than that required to deform the surface of a cornnut.

In a eleventh aspect, the invention features new and distinct plant varieties of *Phaseolus vulgaris* characterized by early maturity, bush type growth habit, synchronous fruiting, photoperiod insensitivity and which produce a popping bean.

In a twelfth aspect, the invention features a bean plant developed through hybridization characterized by genetic factors which confer early maturity, bush type growth habit, synchronous fruiting, photoperiod insensitivity, and production of a popping bean.

In a thirteenth aspect, the invention features a method of producing beans comprising self-pollinating a bean plant of the species *Phaseolus vulgaris* which exhibits the phenotypic characteristics of early maturity, bush type growth habit, synchronous fruiting, photoperiod insensitivity, and which produces a popping bean.

In a fourteenth aspect, the invention features a novel process to produce the seeds of a bean plant which exhibits the phenotypic characteristics of early maturity, bush type growth habit, synchronous fruiting, photoperiod insensitivity, and which produces a popping bean comprising the steps of: (a) crossing plants grown from the seeds of a nuña accession and a *Phaseolus vulgaris* cultivar exhibiting the characteristics of early maturity, bush type growth habit, synchronous fruiting, photoperiod insensitivity; (b) developing a pure plant line from the seeds produced in (a), the plant line being selected for early maturity, bush type growth habit, synchronous fruiting, photoperiod insensitivity, and the ability to produce a popping bean; and (c) harvesting the seeds of the pure plant variety which exhibits the phenotypic characteristics of early maturity, bush type growth habit, synchronous fruiting, photoperiod insensitivity, and which produces popping beans.

In preferred embodiments the nuña accession is selected from the group consisting of accession numbers W6 4296, W6 4297, W6 4298, PI 298820, PI 298822, PI 298824, PI 316013, PT 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402; the *Phaseolus vulgaris* cultivar is selected from the group consisting of small white, small red, navy, dark red kidney, light red kidney, black or black turtle, pink, pinto, cranberry, and canario.

In a fifteenth aspect, the invention features a novel process to produce the seeds of a bean plant which exhibits the phenotypic characteristics of early maturity, bush type growth habit, synchronous fruiting, photoperiod insensitivity, and which produces a popping bean comprising the steps of: (a) crossing plants grown from the seeds of first nuña accession and a *Phaseolus vulgaris* cultivar exhibiting the characteristics of early maturity, bush type growth habit, synchronous fruiting, photoperiod insensitivity; (b) developing a pure plant line from the seeds produced in (a), the plant line being selected for early maturity, bush type growth habit, synchronous fruiting, and the ability to produce popping beans; (c) crossing plants grown from the seeds of a second nuña accession and the *Phaseolus vulgaris* cultivar exhibiting the characteristics of early maturity, bush type growth habit, synchronous fruiting, photoperiod insensitivity to develop $F_1$ plants; (d) crossing plants of the plant line of step (b) with said $F_1$ plants of step (c); (e) developing a pure plant line from the seeds produced in (d), the plant line being selected for early maturity, bush type growth habit, synchronous fruiting, photoperiod insensitivity, and the ability to produce a popping bean; and (f) harvesting the seeds of the pure plant variety which exhibits the phenotypic characteristics of early maturity, bush type growth habit, synchronous fruiting, photoperiod insensitivity, and which produces popping beans.

In preferred embodiments, the first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402; the *Phaseolus vulgaris* cultivar is selected from the group consisting of small white, small red, navy, dark red kidney, light red kidney, black or black turtle, pink, pinto, cranberry, and canario.

In a sixteenth aspect, the invention features a novel process to produce the seeds of a bean plant which exhibits the phenotypic characteristics of early maturity, bush type growth habit, synchronous fruiting, photoperiod insensitivity, and which produces a popping bean comprising the steps of: (a) crossing plants grown from the seeds of the Nuña accession No. PI316013 and California Early Light Red Kidney; (b) developing a pure plant line from the seeds produced in (a), the plant line being selected for early maturity, bush type growth habit, synchronous fruiting, and the ability to produce popping beans; (c) crossing plants grown from the seeds of the Nuña accession No. PI316032 and California Early Light Red Kidney to develop $F_1$ plants; (d) crossing plants of the plant line of step (b) with the $F_1$ plants of step (c); (e) developing a pure plant line from the seeds produced in (d), the plant line being selected for early maturity, bush type growth habit, synchronous fruiting, photoperiod insensitivity, and the ability to produce a popping bean; and (f) harvesting the seeds of the pure plant variety which exhibits the phenotypic characteristics of early maturity, bush type growth habit, synchronous fruiting, photoperiod insensitivity, and which produces popping beans.

In a seventeenth aspect, the invention features seed produced by (a) crossing plants grown from the seeds of a nuña accession and a *Phaseolus vulgaris* cultivar exhibiting the characteristics of early maturity, bush type growth habit, synchronous fruiting, photoperiod insensitivity; (b) developing a pure plant line from the seeds produced in (a), the plant line being selected for early maturity, bush type growth habit, synchronous fruiting, photoperiod insensitivity, and the ability to produce a popping bean; and (c) harvesting the seeds of the pure plant variety which exhibits the phenotypic characteristics of early maturity, bush type growth habit, synchronous fruiting, photoperiod insensitivity, and which produces popping beans.

In preferred embodiments the nuña accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402; the *Phaseolus vulgaris* cultivar is selected from the group consisting of small white, small red, navy, dark red kidney, light red kidney, black or black turtle, pink, pinto, cranberry, and canario.

In an eighteenth aspect, the invention features seeds produced by (a) crossing plants grown from the seeds of first nuña accession and a *Phaseolus vulgaris* cultivar exhibiting the characteristics of early maturity, bush type growth habit, synchronous fruiting, photoperiod insensitivity; (b) developing a pure plant line from the seeds produced in (a), the plant line being selected for early maturity, bush type growth habit, synchronous fruiting, and the ability to produce popping beans; (c) crossing plants grown from the seeds of a second nuña accession and the *Phaseolus vulgaris* cultivar exhibiting the characteristics of early maturity, bush type growth habit, synchronous fruiting, photoperiod insensitivity to develop $F_1$ plants; (d) crossing plants of the plant line of step (b) with the $F_1$ plants of step (c); (e) developing a pure plant line from the seeds produced in (d), the plant line being selected for early maturity, bush type growth habit, synchronous fruiting, photoperiod insensitivity, and the ability to produce a popping bean; and (f) harvesting the seeds of the pure plant variety which exhibits the phenotypic characteristics of early maturity, bush type growth habit, synchronous fruiting, photoperiod insensitivity, and which produces popping beans.

In preferred embodiments, the first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402; the *Phaseolus vulgaris* cultivar is selected from the group consisting of small white, small red, navy, dark red kidney, light red kidney, black or black turtle, pink, pinto, cranberry, and canario.

In a ninetenth aspect, the invention features seeds produced by (a) crossing plants grown from the seeds of the Nuña accession No. PI316013 and California Early Light Red Kidney; (b) developing a pure plant line from the seeds produced in (a), the plant line being selected for early maturity, bush type growth habit, synchronous fruiting, and the ability to produce popping beans; (c) crossing plants grown from the seeds of the Nuña accession No. PI316032 and California Early Light Red Kidney to develop $F_1$ plants; (d) crossing plants of the plant line of step (b) with plants of step (c); (e) developing a pure plant line from the seeds produced in (d), the plant line being selected for early maturity, bush type growth habit, synchronous fruiting, photoperiod insensitivity, and the ability to produce a popping bean; and (f) harvesting the seeds of the pure plant variety which exhibits the phenotypic characteristics of early maturity, bush type growth habit, synchronous fruiting, photoperiod insensitivity, and which produces popping beans.

In a twentieth aspect, the invention features progeny plants produced from the seeds of claims 8, 9, 10, 11, 12, 13, 14, 15, 28, 29, or 30.

In a twenty-first aspect, the invention features a plant cell derived from the plant or a progeny plant of claims 1, 18, 9, or 31.

The present invention also contemplates progeny plants or plant cells produced from the seed or plants of the present invention. The progeny plants or progeny plant cells may be produced using art recognized in vivo, in vitro and breeding methods. Progeny as used herein refers to any descendant, including a descendant removed by many generations from a particular related plant.

The present invention also contemplates variants, mutants and modifications of the claimed bean plants including improvements such as a higher percentage of popping of beans, greater yield, improved favor, improved texture and pest resistance. Such improvements are possible by using standard plant breeding procedures.

Figure 1:
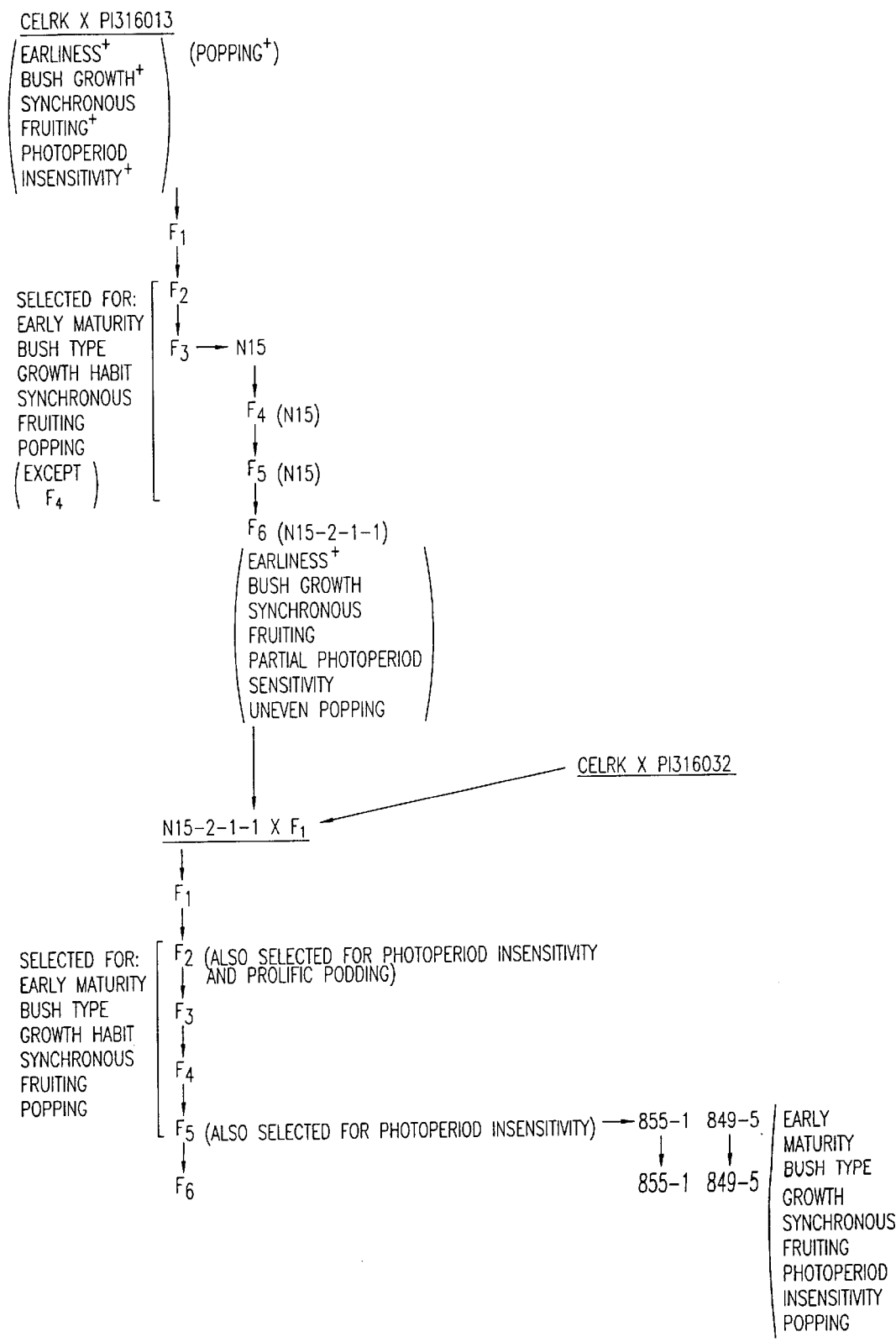
FIG. 1 is a representation of the crosses and selfs carried out to produce a *Phaseolus vulgaris* plant "popping bean"

species which exhibits early maturity, bush type growth habit, synchronous fruiting and photoperiod insensitivity.

DESCRIPTION OF THE PREFERRED EMBODIMENTS

The following Example is provided for further illustrating various aspects and embodiments of the present invention and is in no way intended to be limiting in scope.

EXAMPLE 1

Production of a *Phaseolus vulgaris* Plant "Popping Bean" Species which Exhibits Early Maturity, Bush Type Growth Habit, Synchronous Fruiting and Photoperiod Insensitivity The methods utilized to produce the bean plants of the present invention are traditional plant breeding procedures and the pedigree method of plant breeding, all of which are familiar to those who practice the art.

Pedigree breeding and recurrent selection breeding methods are used to develop inbred lines from breeding populations. Breeding programs combine desirable traits from two or more inbred lines or various broad based sources into breeding pools from which new inbred lines are developed by selfing and the selection of desired phenotypes.

Pedigree breeding starts with the crossing of two genotypes, each of which may have one or more desirable characteristics that is lacking in the other or which complement the other. In pedigree breeding method, the superior plants of the segregating generations are identified, selfed and selected in successive generations. In the succeeding generations the heterozygous condition gives way to homogeneous lines as the result of self-pollination and selection. Typically in the pedigree method of plant breeding five or more generations of selfing and single plant selection is practiced.

The following scheme was used to combine the desired traits of early maturity, bush type growth habit, synchronous fruiting, photoperiod insensitivity, and the ability to produce beans that pop into genotypes well adapted to bean growing regions in the United States (see FIG. 1). Twelve different crosses between Nuñas and United States cultivars were made and a large number of individuals and lines were evaluated for the desired traits. The scheme described below is only one scheme which resulted in the development of two lines that exhibited the preferred traits. One of skill in the art will understand that the particular order, number and duration of the breeding steps may be varied and still produce a plant of the present invention. Another scheme useful to produce the plants of the present invention is a single cross of a nuña accession and a *Phaseolus vulgaris* cultivar exhibiting the characteristics of early maturity, bush type growth habit, synchronous fruiting, and photoperiod insensitivity followed by selection of a large number of $F_2$ individuals for the desired traits.

Further, one of skill in the art will understand that equivalents to the particular plants used in the breeding process may be available and used to produce the plants of the present invention. Nuñas that are useful in the present invention are those that pop or expand upon heating. In addition to those already discussed these include, but are not limited to, accession numbers W6 4296, W6 4297, W6 4298, PI 298820, PI 298822, PI 298824, PI 316014, PI 316016, PI 316017, PI 316018, PI 316019, PI 316020, PI 316021, PI 316022, PI 316023, PI 316024, PI 316025, PI 316029, PI 316030, PI 316031, PI 390771, PI 390775, PI 511763, PI 511767, PI 531862, PI 577677, PI 577678, PI 577679, PI 577680, PI 577682, and PI 608402. *Phaseolus vulgaris* cultivars that are useful in the present invention include those that exhibit the characteristics of early maturity, bush type growth habit, synchronous fruiting, and photoperiod insensitivity. For example, such *Phaseolus vulgaris* cultivars include but are not limited to small white, small red, navy, dark red kidney, light red kidney, black or black turtle, pink, pinto, cranberry, and canario. Andean gene pool germplasm is preferred. One of ordinary skill in the art will understand that within the above listed market classes of *Phaseolus vulgaris* cultivars there are many varieties, such as pink: Sutter Pink and Telano; light red kidney: Linden and California Early Light Red; dark red kidney: California Dark Red Kidney and Montcalm; pinto: NW 590, Othello, RNK 101, UI 196, Flint, Fiesta, UI 126, UI 129, Olathe, UI 114; small white: Aurora; small red: Ruffus and Red Mexican; black: Black Turtle Soup 39, Midnight, Blackhawk, and Raven; navy: Huron, Avanti, Fleetside, Seafarer, Albion, and Midland; cranberry: Taylor. These varieties and the like are also useful in the present invention. Such varieties are readily ascertainable, for example from listings by the U.S. Department of Agriculture and from generally available commercial sources.

Cross California Early Light Red Kidney to PI316013 (Home Greenhouse), Spring 1992.

Hybridization of the Peruvian nuña accession No. PI316013 with the early maturing red kidney variety 'California Early Light Red Kidney'. A kidney cultivar was chosen as one parent since both parents would then be members of the Andean genepool of common bean and therefore the progeny should have higher performance than inter-genepool crosses such as between Andean x Meso-American genepools. Also, the kidney cultivar would be a donor of the traits of early maturity, bush type growth habit, synchronous fruiting and photoperiod insensitivity.

Advance $F_1$ to Obtain $F_2$ Seed (Home Greenhouse), Summer 1992

Plant $F_2$ to Obtain $F_3$ (Home Greenhouse), Fall 1992

Approximately 200 $F_2$ plants were grown, selected for early maturity, bush type growth habit, synchronous fruiting and evaluated for popping at maturity.

Four methods, hot air, microwave, hot skillet and deep frying in oil, were used to initially screen for the ability to pop. All methods were successfully used to pop the beans of the current invention. However, hot air and frying gave the highest percent popped beans and the most uniform product. Hot-air was chosen as the preferred screening method as this was the method envisioned to be most likely method adopted to commercially produce a low-fat popped bean product.

A modified hot-air popcorn popper (Presto) was used to screen seeds from individual $F_2$ plants. Ten seeds form each $F_2$ plant were placed in the pre-warmed popper for 1.5 minutes, after which the sample was visually inspected for frequency of popped beans and extent of expansion. Remnant seed of $F_2$ individuals with the highest percent of popped beans and greatest expansion were selected for further evaluation. A similar protocol was used to evaluate ability to pop in subsequent generations. Popping was carried out at a moisture level of about 9 to 10%. Applicants have discovered that the percentage of moisture is a significant factor in determining the ability of the beans to pop. Popping is substantially reduced above 12% moisture and below 5%. Moisture is measured on a dry weight basis by weighing a sample of seeds at the time of popping after drying for 3 days at 105° C.

Plant Selected $F_3$(N15) Obtain $F_4$ (Home Greenhouse), Spring 1993

Approximately 20 $F_2$ plants were selected for early maturity, bush type growth habit, synchronous fruiting and identified as producing beans that exhibited popping. About 10 $F_3$ plants from each of the 20 single plant selections were grown. Ten single plant selections were made from 5 of the $F_3$ families. $F_3$ family No. 15 (N15) was an elite appearing family and several single-plant selections were made from it.
Sent Ten Selected $F_4$ Families for Increase and Inbreeding to Hawaii (Hawaiian Research Ltd., Molakai), Summer 1993.

The ten $F_4$ families (which included five N15 selections) were sent to Hawaii for increase and inbreeding. The N15 lines produced seed in less than 100 days. The seed from each family was bulked and sent back to California.
Grew Ten $F_5$ Bulks (La Sierra Greenhouse),Winter 1993.

The ten bulk $F_5$ families were grown in the greenhouse during the Winter of 1993. Single plant selections (early maturity, bush type growth habit, and synchronous fruiting) were made from each family and evaluated for popping. The $F_6$ line N15-2-1-1 was among the selections made. This line possessed earliness, bush type growth and synchronous fruiting, but exhibited uneven popping characteristics and only moderate yield potential due in part to partial photoperiod sensitivity with respect to reproductive development. Under high temperature, long day conditions, bean lines with partial photoperiod sensitivity exhibited arrested floral bud development and few pods are set.
Cross $F_1$ of PI316032 x CELRK with N15-2-1-1

California Early Light Red Kidney was hybridized with PI316032 (a Peruvian nuña accession with excellent popping characteristics). This $F_1$ was then crossed with N15-2-1-1 in order to transfer additional genes or modifier genes for popping from PI316032 and more complete photoperiod insensitivity and local adaption from CELRK to N15-2-1-1. The use of this three-way cross allowed simultaneous improvement of popping and adaptation in a single cross.
Advance $F_1$ (Del Valle Date Gardens-Indio), Spring 1994

Ten plants of this three-way cross $F_1$ were advanced and approximately 1000 $F_2$ seeds were obtained and bulked.
Plant $F_2$ (Rheingans Ranch-Temecula), Summer 1994.

The $F_2$ population of this cross was grown under long photoperiod conditions. Plants were visually selected at maturity for the desired combination of adaptive/agronomic traits (early maturity, bush type growth habit, synchronous fruiting and photoperiod insensitivity), as well as for prolific podding. Popping ability of 400 selections was again evaluated in a hot air corn popping machine. Because the inheritance (number of genes, dominance, and existence of epistasis and modifiers) of the popping trait was not known, a large number of single-plant selections were evaluated for their popping characteristics. About 40 individuals exhibiting the best popping characteristics were selected.
Plant Selected $F_3$ (Home Greenhouse), Fall 1994.

The 40 $F_3$ families were planted in the greenhouse with 10 individuals per family. Another round of single-plant selection was conducted for early maturity, bush type growth habit, synchronous fruiting and the ability to pop. About 200 individuals were evaluated for popping using a hot air popper.
Plant Selected $F_4$ Families (U. C. Riverside Coachella Valley Agricultural Research Station), Spring 1995.

Thirty-five $F_4$ families were grown in single row plots 20 feet long. Single plant selection was conducted again for adaptation and agronomic characteristics (early maturity, bush type growth habit, and synchronous fruiting). Selection for the ability to pop was then conducted with a hot air corn popper on about one hundred selections. Twenty-one families were selected.
Plant the Selected Twenty-one $F_5$ Families (U. C. Riverside Field Station, Field 9A), Summer 1995.

The 21 families were planted in single row plots, 20 feet long. Selection for agronomic characteristics (early maturity, bush type growth habit, synchronous fruiting and photoperiod insensitivity) and for the ability pop was conducted. Two $F_5$ families were selected for multiplication (Selection from Field 9A rows 849 and 855)and the seed bulked. These are 849-5 which have solid dark red, medium sized, (0.32 mg/seed) grain and 855-1 which have white with dark purple speckling, medium sized (0.35 mg/seed) grain. These families exhibit the desired traits of early maturity, bush type growth habit, synchronous fruiting, photoperiod insensitivity and produce popping beans.
Seed Increase $F_6$ (Home Greenhouse), Fall, 1995 and Spring, 1996
Seed Increase of 849-5 and 855-1 (Tarke plot, Tom Stine, grower, Meridian, Calif.), Summer 1996
Seed Increase of 849-5 (Muleshoe, Tex.,) Summer 1996
Seed Increase of 849-5 and 855-1 (Indio, Joe Manion grower), Spring 1997.

Nine acres of each variety were grown.

Other embodiments are within the claims.

What is claimed is:

1. A bean plant of the species *Phaseolus vulgaris* which exhibits the phenotypic characteristics of early maturity, bush type growth habit, synchronous fruiting, photoperiod insensitivity, and which produces a bean that pops at a moisture of about 5 to 12 percent.

2. The plant of claim 1, wherein said early maturity is a growing season of no greater than 100 days in which said plant reaches the dry pod stage.

3. The plant of claim 1, wherein said photoperiod insensitivity is the ability to flower when daylengths are greater than or equal to 13 hours.

4. The plant of claim 1, wherein said bush type growth habit encompasses a height of less than 0.75 meter.

5. Plant parts derived from a plant of claims 1–4, including leaves, stem, pollen, plant cells and seed.

6. A process for producing a bean plant comprising cultivating the plant of any of claims 1–4.

7. A seed produced from the plant of any of claims 1–4.

8. A bean seed of the species *Phaseolus vulgaris* that germinates into a plant which exhibits the phenotypic characteristics of early maturity, bush type growth habit, synchronous fruiting, photoperiod insensitivity, and which produces a bean that pops at a moisture of about 5 to 12 percent.

9. A bean seed produced by a cross of a nuña accession and a *Phaseolus vulgaris* cultivar exhibiting the characteristics of early maturity, bush type growth habit, synchronous fruiting, and photoperiod insensitivity, wherein said bean pops at a moisture of about 5 to 12 percent.

10. A bean seed of claim 9, wherein said nuña accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402.

11. A bean seed of claim 9, wherein said *Phaseolus vulgaris* cultivar is selected from the group consisting of small white, small red, navy, dark red kidney, light red kidney, black or black turtle, pink, pinto, cranberry, and canario.

12. A bean seed that pops at a moisture of about 5 to 12 percent produced by a first, second and third cross comprising:
   a first cross of a first nuña accession and a *Phaseolus vulgaris* cultivar exhibiting the characteristics of early maturity, bush type growth habit, synchronous fruiting, and photoperiod insensitivity;
   a second cross of a second nuña accession and said *Phaseolus vulgaris* cultivar exhibiting the characteristics of early maturity, bush type growth habit, synchronous fruiting, and photoperiod insensitivity; and
   a third cross of the offspring of said first and second crosses, wherein the bean seed produced from the offspring of third cross pops at a moisture of about 5 to 12 percent.

13. A bean seed of claim 12, wherein said first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402.

14. A bean seed of claim 12, wherein said *Phaseolus vulgaris* cultivar is selected from the group consisting of small white, small red, navy, dark red kidney, light red kidney, black or black turtle, pink, pinto, cranberry, and canario.

15. A bean seed from the bean plant of claim 1 produced by a first cross of nuña accession No. PI 316013 and a California Early Light Red Kidney line;
   a second cross of nuña accession No. PI 316032 and a California Early Light Red Kidney line; and
   a third cross of the offspring of said first and second crosses.

16. A bean that pops at a moisture of about 5 to 12 percent produced from a plant of the species *Phaseolus vulgaris* which exhibits early maturity, bush type growth habit, synchronous fruiting, and photoperiod insensitivity.

17. A popped bean from a plant of the species *Phaseolus vulgaris*, said plant characterized by early maturity, bush type growth habit, synchronous fruiting, photoperiod insensitivity, and which produces a bean that pops at a moisture of about 5 to 12 percent, that exhibits a texture less than that exhibited by a corn nut.

18. Plant varieties of *Phaseolus vulgaris* characterized by early maturity, bush type growth habit, synchronous fruiting, photoperiod insensitivity and which produce a bean that pops at a moisture of about 5 to 12 percent.

19. A *Phaseolus vulgaris* bean plant developed through hybridization characterized by genetic factors which confer early maturity, bush type growth habit, synchronous fruiting, photoperiod insensitivity, and the production of a bean that pops at a moisture of about 5 to 12 percent.

20. A method of producing beans comprising self-pollinating a bean plant of the species *Phaseolus vulgaris* which exhibits the phenotypic characteristics of early maturity, bush type growth habit, synchronous fruiting, photoperiod insensitivity, and which produces a bean that pops at a moisture of about 5 to 12 percent.

21. A process to produce the seeds of a bean plant which exhibits the phenotypic characteristics of early maturity, bush type growth habit, synchronous fruiting, photoperiod insensitivity, and which produces a bean that pops at a moisture of about 5 to 12 percent comprising the steps of:

(a) crossing plants grown from the seeds of a nuña accession and a *Phaseolus vulgaris* cultivar exhibiting the characteristics of early maturity, bush type growth habit, synchronous fruiting, and photoperiod insensitivity;
   (b) developing a pure plant line from the seeds produced in (a), said plant line being selected for early maturity, bush type growth habit, synchronous fruiting, photoperiod insensitivity, and the production of a bean that pops at a moisture of about 5 to 12 percent; and
   (c) harvesting the seeds of said pure plant line which exhibits the phenotypic characteristics of early maturity, bush type growth habit, synchronous fruiting, photoperiod insensitivity, and which produces a bean that pops at a moisture of about 5 to 12 percent.

22. The process of claim 21, wherein said nuña accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402.

23. The process of claim 21, wherein said *Phaseolus vulgaris* cultiver is selected from the group consisting of small white, small red, navy, dark red kidney, light red kidney, black or black turtle, pink, pinto, cranberry, and canario.

24. A process to produce the seeds of a bean plant which exhibits the phenotypic characteristics of early maturity, bush type growth habit, synchronous fruiting, photoperiod insensitivity, and which produces a bean that pops at a moisture of about 5 to 12 percent comprising the steps of:

(a) crossing plants grown from the seeds of a first nuña accession and a *Phaseolus vulgaris* cultivar exhibiting the characteristics of early maturity, bush type growth habit, synchronous fruiting, and photoperiod insensitivity;
   (b) developing a pure plant line from the seeds produced in (a), said plant line being selected for early maturity, bush type growth habit, synchronous fruiting, photoperiod insensitivity and the production of a bean that pops at a moisture of about 5 to 12 percent;
   (c) crossing plants grown from the seeds of a second nuña accession and said *Phaseolus vulgaris* cultivar exhibiting the characteristics of early maturity, bush type growth habit, synchronous fruiting, and photoperiod insensitivity to develop $F_1$ plants;
   (d) crossing plants of the plant line of step (b) with said $F_1$ plants of step (c);
   (e) developing a pure plant line from the seeds produced in (d), said plant line being selected for early maturity, bush type growth habit, synchronous fruiting, photoperiod insensitivity and the production of a bean that pops at a moisture of about 5 to 12 percent; and
   (f) harvesting the seeds of said pure plant line which exhibits the phenotypic characteristics of early maturity, bush type growth habit, synchronous fruiting, photoperiod insensitivity, and which produces a bean that pops at a moisture of about 5 to 12 percent.

25. The process of claim 24, wherein said first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and PI 608402.

26. The process of claim 24, wherein said *Phaseolus vulgaris* cultivar is selected from the group consisting of small white, small red, navy, dark red kidney, light red kidney, black or black turtle, pink, pinto, cranberry, and canario.

27. A process to produce the seeds of a bean plant which exhibits the phenotypic characteristics of early maturity, bush type growth habit, synchronous fruiting, photoperiod insensitivity, and which produces a bean that pops at a moisture of about 5 to 12 percent comprising the steps of:

(a) crossing plants grown from the seeds of nuña accession No. PI 316013 and a California Early Light Red Kidney line;

(b) developing a pure plant line from the seeds produced in (a), said plant line being selected for early maturity, bush type growth habit, synchronous fruiting, photoperiod insensitivity and the production of a bean that pops at a moisture of about 5 to 12 percent;

(c) crossing plants grown from the seeds of nuña accession No. PI 316032 and a California Early Light Red Kidney line to develop $F_1$ plants;

(d) crossing plants of the plant line of step (b) with said $F_1$ plants of step (c);

(e) developing a pure plant line from the seeds produced in (d), said plant line being selected for early maturity, bush type growth habit, synchronous fruiting, photoperiod insensitivity and the production of a bean that pops at a moisture of about 5 to 12 percent; and (f) harvesting the seeds of said pure plant line which exhibits the phenotypic characteristics of early maturity, bush type growth habit, synchronous fruiting, photoperiod insensitivity, and which produces a bean that pops at a moisture of about 5 to 12 percent.

28. Seeds produced according to the process of claim 21.

29. Seeds produced according to the process of claim 24.

30. Seeds produced according to the process of claim 27.

31. Progeny plants having the desired characteristics of and produced from the seeds of claims 8, 9, 10, 11, 12, 13, 14, 15, 28, 29 or 30.

32. A plant cell derived from the plant or a progeny plant of claims 1, 18, or 19.

33. A plant cell derived from the plant or a progeny plant of claim 31.

* * * * *

UNITED STATES PATENT AND TRADEMARK OFFICE
CERTIFICATE OF CORRECTION

PATENT NO : 6,040,503
DATED : March 21, 2000
INVENTOR(S) : Ehlers et al.

It is certified that error appears in the above-identified patent and that said Letters Patent is hereby corrected as shown below:

In the References Cited section, before PUBLICATIONS, please insert:

U.S. PATENT DOCUMENTS

| | | |
|---|---|---|
| 5,183,678 | 02/02/93 | Taga et al. |
| 3,650,763 | 03/21/72 | Touba |
| 4,006,260 | 02/01/77 | Webb et al. |
| 4,585,660 | 04/29/86 | Sugisawa et al. |
| 4,877,637 | 10/31/89 | Harp |
| 3,754,930 | 08/28/73 | Toei et al. |
| 3,661,071 | 05/09/72 | Toei et al. |
| 3,738,848 | 06/12/73 | Mader |
| 4,891,235 | 01/02/90 | Mizuguchi et al. |
| 5,326,583 | 07/05/94 | Taga et al. |
| 2,278,475 | 04/07/42 | Musher |

Signed and Sealed this

Fifteenth Day of May, 2001

*Attest:*

NICHOLAS P. GODICI

*Attesting Officer*   *Acting Director of the United States Patent and Trademark Office*